(12) United States Patent
Izumi (10) Patent No.: US 7,686,772 B2
(45) Date of Patent: Mar. 30, 2010

(54) APPARATUS FOR MEASURING CALORIES CONSUMED DURING SLEEP

(75) Inventor: Shuichi Izumi, Asaka (JP)

(73) Assignee: Tanita Corporation, Tokyo (JP)

( * ) Notice: Subject to any disclaimer, the term of this patent is extended or adjusted under 35 U.S.C. 154(b) by 136 days.

(21) Appl. No.: 11/889,667

(22) Filed: Aug. 15, 2007

(65) Prior Publication Data

US 2008/0071196 A1 Mar. 20, 2008

(30) Foreign Application Priority Data

Sep. 19, 2006 (JP) ................................ 2006-252501

(51) Int. Cl.
*A61B 5/103* (2006.01)
(52) U.S. Cl. .................... 600/595; 600/301; 600/483; 600/500
(58) Field of Classification Search ................ 600/300, 600/301, 483, 484, 500, 595
See application file for complete search history.

(56) References Cited

U.S. PATENT DOCUMENTS

| | | | |
|---|---|---|---|
| 4,966,155 A | | 10/1990 | Jackson |
| 5,964,720 A * | | 10/1999 | Pelz ............................ 600/595 |
| 6,030,342 A * | | 2/2000 | Amano et al. ................ 600/301 |
| 6,095,949 A * | | 8/2000 | Arai ............................... 482/4 |
| 6,416,332 B1 * | | 7/2002 | Carron et al. .................. 439/70 |
| 6,485,441 B2 * | | 11/2002 | Woodward .................. 600/595 |
| 7,048,697 B1 * | | 5/2006 | Mitsuru ....................... 600/587 |
| 2003/0226695 A1 * | | 12/2003 | Mault ....................... 177/25.16 |
| 2005/0021110 A1 * | | 1/2005 | Maschke et al. ............... 607/88 |
| 2006/0074326 A1 * | | 4/2006 | Sebastian et al. ............. 600/500 |
| 2006/0161079 A1 * | | 7/2006 | Choi et al. ................... 600/595 |
| 2006/0169282 A1 | | 8/2006 | Izumi et al. |
| 2007/0106183 A1 * | | 5/2007 | Suzuki et al. ................ 600/595 |
| 2007/0282176 A1 * | | 12/2007 | Shimada et al. ............. 600/300 |

FOREIGN PATENT DOCUMENTS

| | | |
|---|---|---|
| JP | 2003-164496 | 6/2003 |
| WO | WO 86/04497 | 8/1986 |

OTHER PUBLICATIONS

Chinese Office Action issued in Chinese Patent Application No. CN 2007101518234, mailed Jan. 9, 2009.
European Search Report issued in European Patent Application No. 07016375.3-2319/ 1902674 dated on Jul. 1, 2008.

* cited by examiner

*Primary Examiner*—Patricia C Mallari
*Assistant Examiner*—Karen E Toth
(74) *Attorney, Agent, or Firm*—McDermott Will Emery LLP (57) ABSTRACT

An apparatus for measuring calories consumed during sleep comprises determination means for determining a breathing/heartbeat oscillation, a body motion and an the intensity of the body motion, coefficient calculation means for calculating a coefficient which is a reference value for calculating calories consumed during sleep, based on the signals in a given period of breathing/heartbeat oscillation and a sleep metabolic rate, consumed calorie calculation means for calculating calories consumed during sleep, based on consumed calories according to the magnitude of each signal and the coefficient, and storage means for storing various arithmetic expressions in advance. Accordingly, the present apparatus makes it possible to acquire calories consumed by the motions of the body of an individual subject in more detail and to measure calories consumed during sleep more accurately.

2 Claims, 9 Drawing Sheets

| Select ID, please. | |
|---|---|
| ID : 1 | ID : 6 |
| ID : 2 | ID : 7 |
| ID : 3 | ID : 8 |
| ID : 4 | ID : 9 |
| ID : 5 | FIRST |

FIG. 5B

| Select Sex, please. | |
|---|---|
| Sex | Female |
| Age | |
| Height(cm) | |
| Weight(kg) | |
| Epoch(sec) | |

FIG. 5C

| Input Age, please. | |
|---|---|
| Sex | Female |
| Age | 45 |
| Height(cm) | |
| Weight(kg) | |
| Epoch(sec) | |

FIG. 5D

| Input Height, please. | |
|---|---|
| Sex | Female |
| Age | 45 |
| Height(cm) | 158 |
| Weight(kg) | |
| Epoch(sec) | |

FIG. 5E

| Input Weight, please. | |
|---|---|
| Sex | Female |
| Age | 45 |
| Height(cm) | 158 |
| Weight(kg) | 51 |
| Epoch(sec) | |

FIG. 5F

| Input Epoch, please. | |
|---|---|
| Sex | Female |
| Age | 45 |
| Height(cm) | 158 |
| Weight(kg) | 51 |
| Epoch(sec) | 60 |

FIG. 5G

| Data, OK ? | |
|---|---|
| Sex | Female |
| Age | 45 |
| Height(cm) | 158 |
| Weight(kg) | 51 |
| Epoch(sec) | 60 |

FIG. 5H

| ID1, OK ? | |
|---|---|
| Sex | Female |
| Age | 45 |
| Height(cm) | 158 |
| Weight(kg) | 51 |
| Epoch(sec) | 60 |

FIG. 5I

| Start, Ready ? | |
|---|---|
| Sex | Female |
| Age | 45 |
| Height(cm) | 158 |
| Weight(kg) | 51 |
| Epoch(sec) | 60 |

FIG. 5J

| Now, Measuring ! | |
|---|---|
| Sex | Female |
| Age | 45 |
| Height(cm) | 158 |
| Weight(kg) | 51 |
| Epoch(sec) | 60 |

FIG. 6

| AMPLITUDE "A" OF BODY MOTION SIGNAL | BODY MOTION |
|---|---|
| $A0 \leq A < A1$ | VERY WEAK |
| $A1 \leq A < A2$ | WEAK |
| $A2 \leq A < A3$ | NORMAL |
| $A3 \leq A$ | STRONG |

APPARATUS FOR MEASURING CALORIES CONSUMED DURING SLEEP

BACKGROUND OF THE INVENTION (i) Field of the Invention

The present invention relates to an apparatus for measuring calories consumed during sleep.

(ii) Description of the Related Art

Heretofore, in a technology disclosed as an apparatus that controls a sleep environment including sleep environment temperature based on the body condition of a user of the apparatus (hereinafter simply referred to as "user"), a technique of calculating calories consumed during sleep from the bioelectrical impedance value, body weight value and information about body oscillations during sleep of the user has been disclosed (for example, refer to Patent Publication 1).

Further, in the same technology as described above, a technique of calculating consumed calories from the skin temperature and sleep stage during sleep of a user has been disclosed (for example, refer to Patent Publication 2).

Patent Publication 1

Japanese Patent Laid-Open Publication No. 2003-164496

Patent Publication 2

Japanese Patent Publication No. 7-114142

However, in the technique described in Patent Publication 1 which estimates information about body oscillations during sleep from a respiration rate and a heart rate, since the intensities (magnitudes) of respiration and heartbeats are not constant, e.g. consumed calories calculated based on deep breathing and consumed calories calculated based on shallow breathing cannot be said to be the same consumed calories even when the number of breaths is the same, it is difficult in some cases to calculate accurate consumed calories only from body oscillation information based on the respiration rate and the heart rate.

Further, in the technique described in Patent Publication 2 which uses a correlation between consumed calories and sleep stages, since it does not take into consideration differences in consumed calories at each sleep stage among individuals, it cannot be said that accurate consumed calories are calculated by the technique.

Therefore, the present invention solves the above problems and provides an apparatus for measuring calories consumed during sleep. The apparatus measures more accurate consumed calories during sleep by determining the magnitudes of body oscillations during sleep and determining calories consumed during sleep from consumed calories based on both body oscillations caused by breathing during sleep and body oscillations caused by heartbeats during sleep (hereinafter referred to as "breathing/heartbeat oscillations") and consumed calories based on the intensities of body oscillations (hereinafter referred to as "body motions") other than the above breathing/heartbeat oscillations during sleep.

SUMMARY OF THE INVENTION

To solve the above problems, the present invention provides an apparatus for measuring calories consumed during sleep which comprises:
input means,
detection means,
calculation means,
determination means,
coefficient calculation means,
consumed calorie calculation means, and
storage means, wherein
the input means inputs the body information of a subject,
the detection means detects body oscillations during sleep,
the calculation means calculates consumed calories based on the body oscillations,
the determination means determines whether each signal of body oscillation during sleep is a signal of breathing/heartbeat oscillation or a signal of body motion and determines the intensity of the body motion,
the coefficient calculation means calculates a coefficient which is a reference value for calculating calories consumed during sleep, based on the signals in a given period of breathing/heartbeat oscillation and a sleep metabolic rate which is obtained based on the input body information,
the consumed calorie calculation means calculates calories consumed during sleep, based on consumed calories according to the magnitude of the signal of breathing/heartbeat oscillation, consumed calories according to the magnitude of the signal of body motion of each intensity and the coefficient,
the storage means stores at least thresholds for making determinations in the determination means, an arithmetic expression for calculating the coefficient and an arithmetic expression for calculating the calories consumed during sleep in advance.

Further, the consumed calorie calculation means calculates an area formed by the waveform of each signal and a baseline which is a basis for waveform formation as the magnitude of each signal.

Further, the consumed calorie calculation means calculates consumed calories according to the magnitude of the signal of body motion of each intensity, based on the total of sampling zones for each body motion intensity and the total of the areas.

An apparatus for measuring calories consumed during sleep according to the present invention comprises:
input means,
detection means,
calculation means,
determination means,
coefficient calculation means,
consumed calorie calculation means, and
storage means, wherein
the input means inputs the body information of a subject,
the detection means detects body oscillations during sleep,
the calculation means calculates consumed calories based on the body oscillations,
the determination means determines whether each signal of body oscillation during sleep is a signal of breathing/heartbeat oscillation or a signal of body motion and determines the intensity of the body motion,
the coefficient calculation means calculates a coefficient which is a reference value for calculating calories consumed during sleep, based on the signals in a given period of breathing/heartbeat oscillation and a sleep metabolic rate which is obtained based on the input body information,
the consumed calorie calculation means calculates calories consumed during sleep, based on consumed calories according to the magnitude of the signal of breathing/heartbeat oscillation, consumed calories according to the magnitude of the signal of body motion of each intensity and the coefficient,
the storage means stores at least thresholds for making determinations in the determination means, an arithmetic expression for calculating the coefficient and an arithmetic expression for calculating the calories consumed during sleep in advance. Accordingly, the present apparatus makes it possible to acquire calories consumed by the motions of the body of an individual subject in more detail and to measure calories consumed during sleep more accurately.

Further, the consumed calorie calculation means calculates an area formed by the waveform of each signal and a baseline which is a basis for waveform formation as the magnitude of each signal. In addition, the consumed calorie calculation means calculates consumed calories according to the magnitude of the signal of body motion of each intensity, based on the total of sampling zones for each body motion intensity and the total of the areas. Consequently, the present apparatus makes it possible not only to measure calories consumed during sleep more accurately but also to make a highly reliable determination even when it is used as a parameter for determining a so-called sleep period or sleep quality.

BRIEF DESCRIPTION OF THE DRAWINGS

FIGS. 5(a) to 5(j) are diagrams illustrating display examples.

DETAILED DESCRIPTION OF THE PREFERRED EMBODIMENTS

An apparatus for measuring calories consumed during sleep according to the present invention comprises:
input means,
detection means,
calculation means,
determination means,
coefficient calculation means,
consumed calorie calculation means, and
storage means, wherein
the input means inputs the body information of a subject,
the detection means detects body oscillations during sleep,
the calculation means calculates consumed calories based on the body oscillations,
the determination means determines whether each signal of body oscillation during sleep is a signal of breathing/heartbeat oscillation or a signal of body motion and determines the intensity of the body motion,
the coefficient calculation means calculates a coefficient which is a reference value for calculating calories consumed during sleep, based on the signals in a given period of breathing/heartbeat oscillation and a sleep metabolic rate which is obtained based on the input body information,
the consumed calorie calculation means calculates calories consumed during sleep, based on consumed calories according to the magnitude of the signal of breathing/heartbeat oscillation, consumed calories according to the magnitude of the signal of body motion of each intensity and the coefficient,
the storage means stores at least thresholds for making determinations in the determination means, an arithmetic expression for calculating the coefficient and an arithmetic expression for calculating the calories consumed during sleep in advance.

Further, the consumed calorie calculation means calculates an area formed by the waveform of each signal and a baseline which is a basis for waveform formation as the magnitude of each signal. In addition, the consumed calorie calculation means calculates consumed calories according to the magnitude of the signal of body motion of each intensity, based on the total of sampling zones for each body motion intensity and the total of the areas.

EXAMPLE 1

Figure 1:
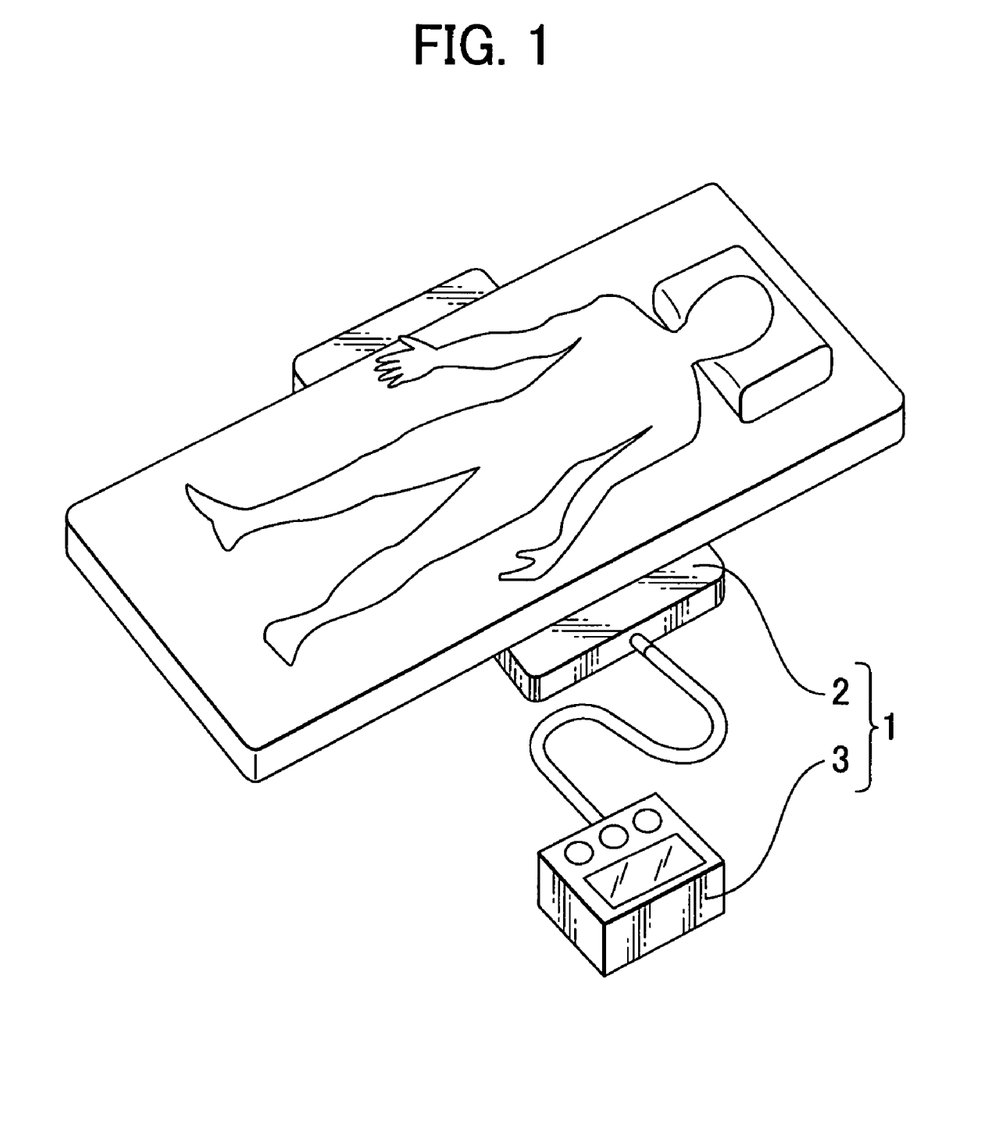
FIG. 1 is an external perspective view of a present apparatus 1.
Figure 2:
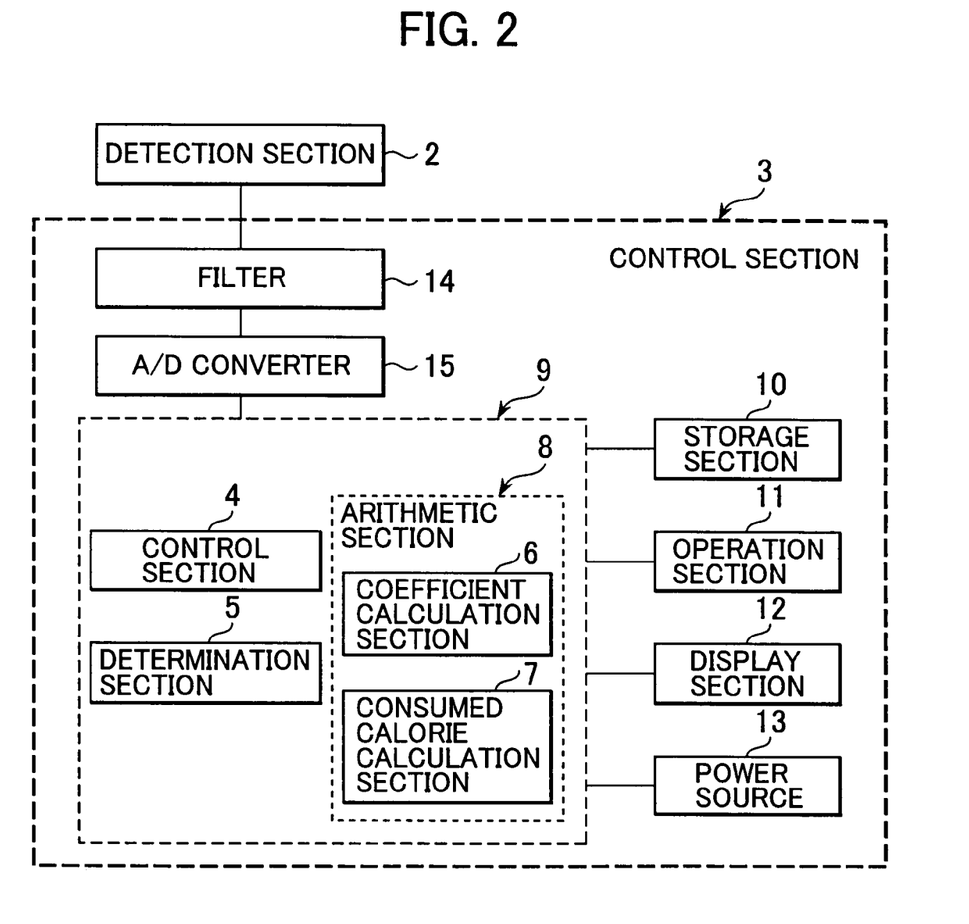
FIG. 2 is a block diagram showing a brief description of the electrical circuit configuration of the present apparatus 1.

Hereinafter, an apparatus 1 for measuring calories consumed during sleep which is an example of the present invention (hereinafter referred to as "present apparatus 1") will be described by use of the drawings. First, the constitution of the present apparatus 1 will be described by use of FIGS. 1 and 2. FIG. 1 is an external perspective view of the present apparatus 1. FIG. 2 is a block diagram showing a brief description of electrical circuit configuration.

The present apparatus 1 comprises a mat-type detection section 2 (hereinafter referred to as "detection section 2") for detecting body oscillations including the above breathing/heartbeat oscillations and body motions of a human body lying on bedding and a control section 3. The control section 3 comprises a CPU 9. The CPU 9 comprises a control section 4 which controls the present apparatus 1, a determination section 5 which determines whether the above detected body oscillation is a breathing/heartbeat oscillation or a body motion and determines the intensities of a waveform signal of the above breathing/heartbeat oscillation (hereinafter referred to as "breathing/heartbeat oscillation signal") and a waveform signal of the above body motion (hereinafter referred to as "body motion signal"), a coefficient calculation section 6 which calculates a coefficient corresponding to a reference value for calculating consumed calories, a consumed calorie calculation section 7 which calculates consumed calories for each measurement epoch based on the intensity of the body motion signal, and an arithmetic section 8 which performs various calculations. Although not shown in the drawings, the CPU 9 also comprises a counter which is known counting means and a timer which is known timing means. Further, in the control section 3, the above CPU 9 is connected to a storage section 10 which stores input ID registration information, detected body oscillation signals, various signals such as breathing/heartbeat oscillation signals and body motion signals, criteria for various determinations on the body motion signals and calculated consumed calorie values, an operation section 11 which comprises a body information input section and a measurement start/end switch, a display section 12 which displays measurement guidance, determination results or calculation results and a power source 13. Further, the CPU 9 is connected to the detection section 2 via a known signal processing filter 14 and A/D converter 15.

Figure 3:
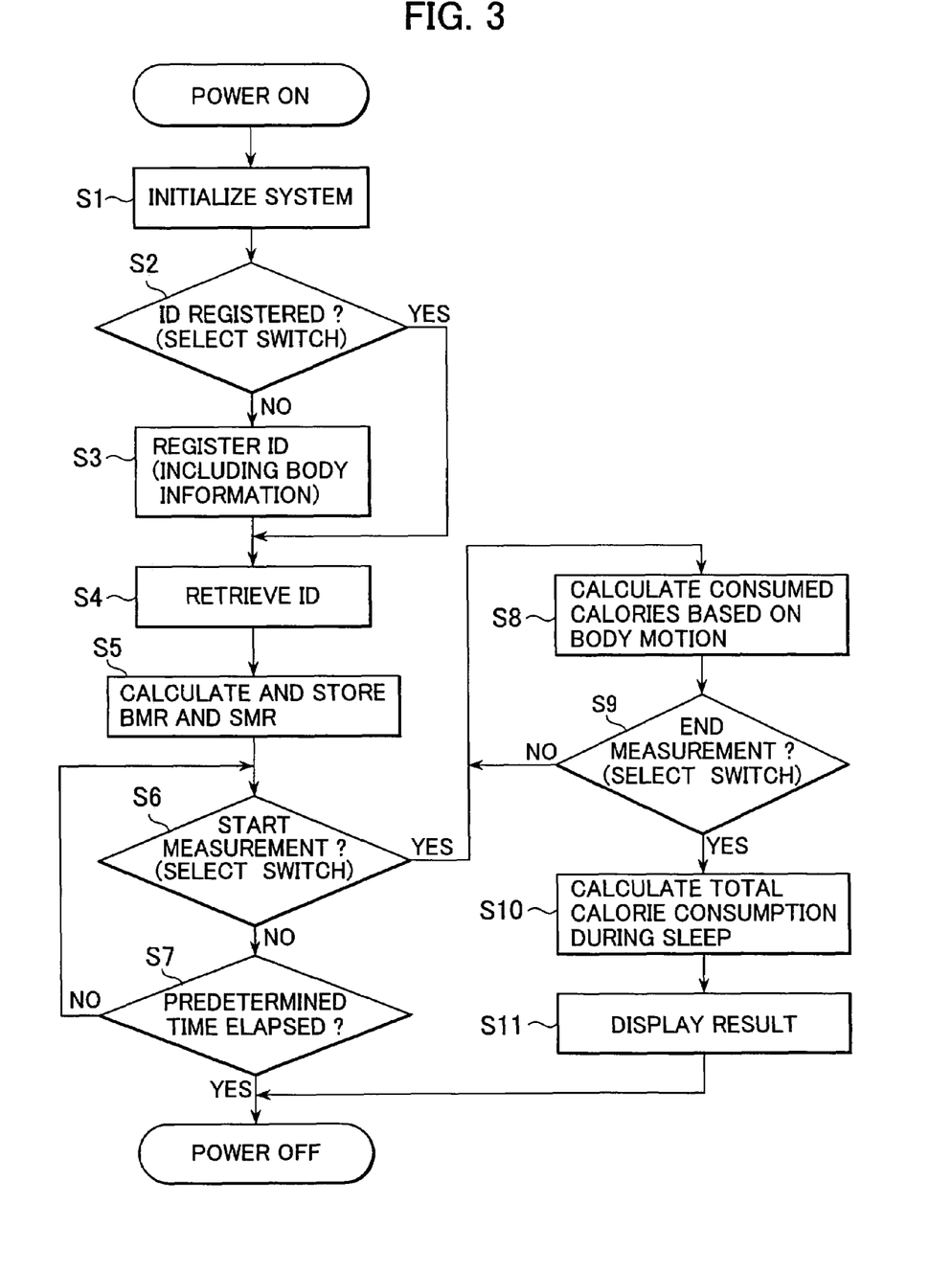
FIG. 3 is a flowchart illustrating main operations in a main routine.
Figure 4:
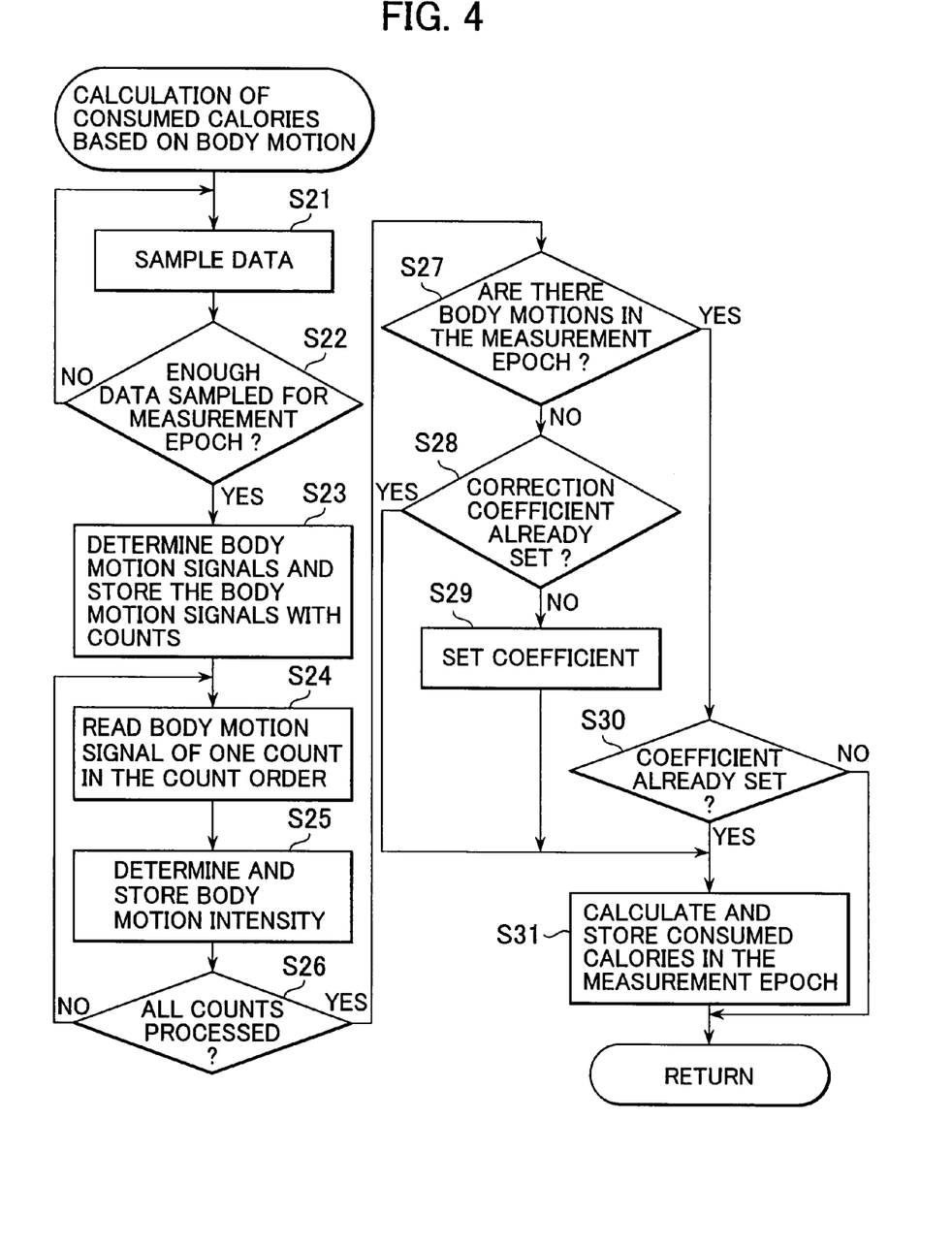
FIG. 4 is a flowchart illustrating operations in a subroutine for calculation of consumed calories based on body oscillations during sleep.
Figure 6:
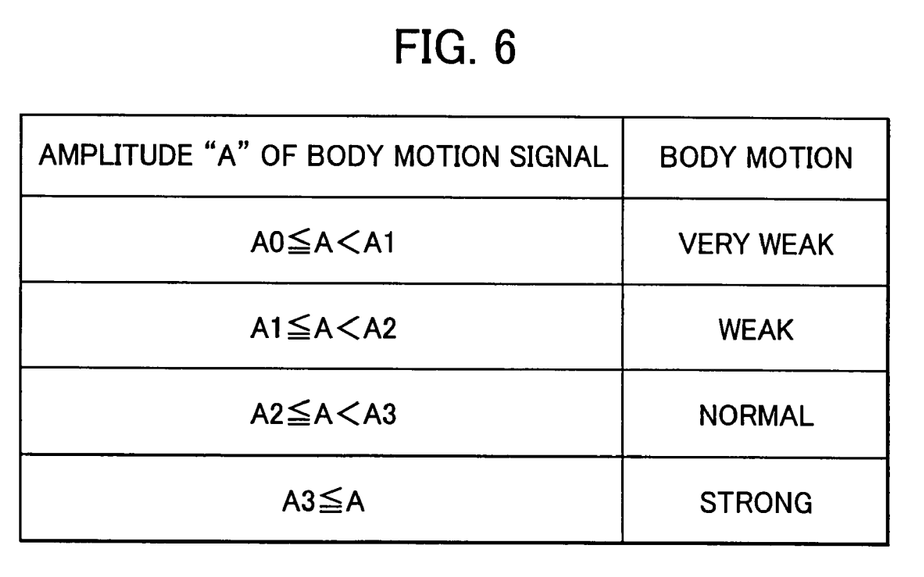
FIG. 6 is a diagram illustrating determination of the intensity of body motion based on the magnitude of a body motion signal.

Next, the operations of the present apparatus 1 will be described by use of FIGS. 3 to 6. FIG. 3 is a flowchart illustrating main operations in a main routine. FIG. 4 is a flowchart illustrating operations in a subroutine for calculation of consumed calories based on body oscillations during sleep. FIGS. 5(a) to 5(j) are diagrams illustrating display examples. FIG. 6 is a diagram illustrating determination of the intensity of body motion based on the magnitude of a body motion signal.

Figure 5A:
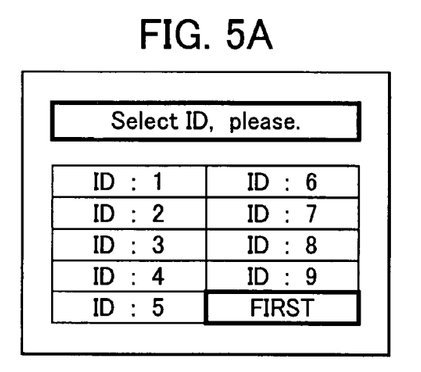
Figure 5B:
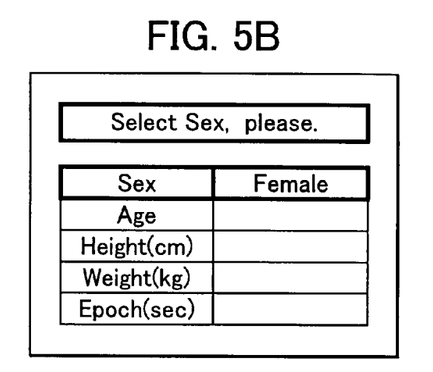
Figure 5C:
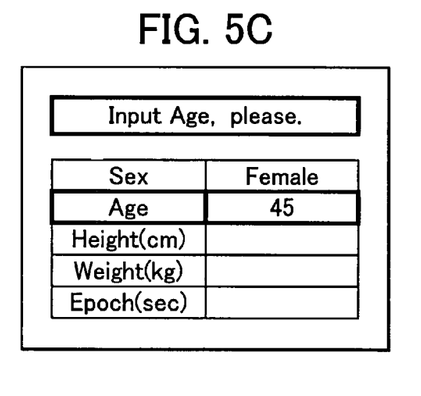
Figure 5D:
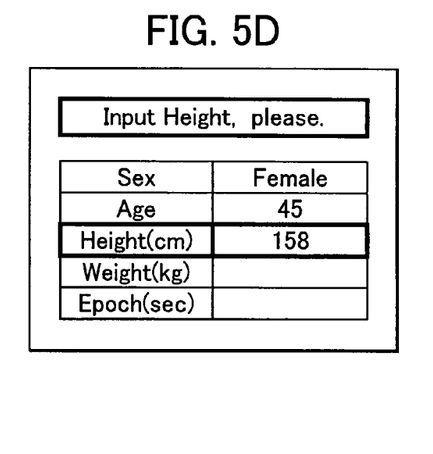
Figure 5E:
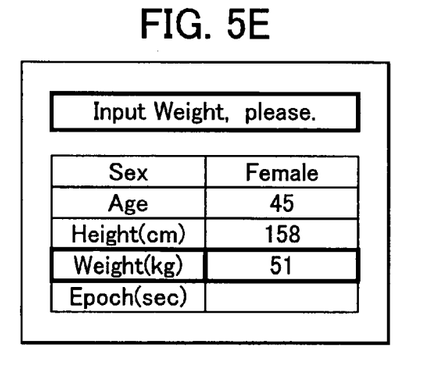
Figure 5F:
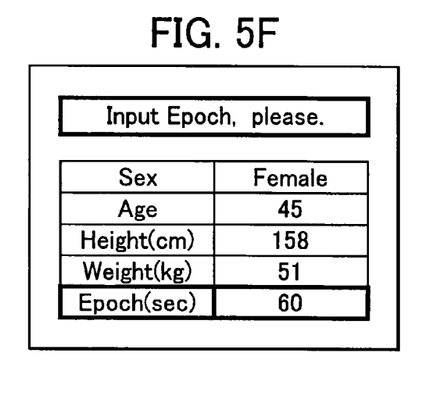
Figure 5G:
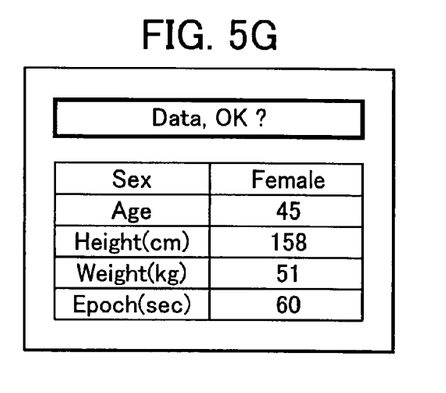
Figure 5H:
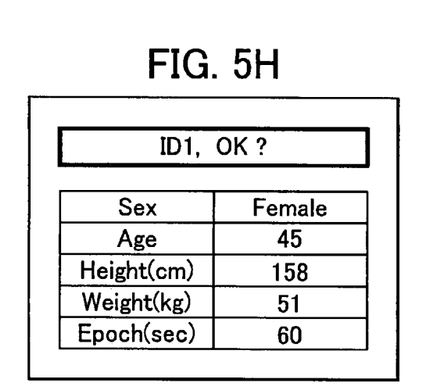

First, operations in the main routine of the present apparatus 1 will be described with reference to the flowchart of FIG. 3. When the power of the present apparatus 1 is turned on, initialization of measurement system is performed in STEP S1, and it is determined in STEP S2 whether an ID for personal authentification has been registered. For example, it is determined whether an ID number selected from a number of ID numbers displayed as in the display example of FIG. 5(a) by use of the operation section 11 has been registered. When the selected ID number has been registered, registered information corresponding to the selected ID number is retrieved from the storage section 10 in STEP S4. Meanwhile, when an unregistered ID number or "First" which is selected when a user conducts a measurement by the present apparatus 1 for the first time has been selected, a user enters body information by use of the operation section 11 in accordance with guidance as in the display examples of FIGS. 5(b) to 5(g) for ID registration in STEP S3. Upon completion of the registration, the registered information is retrieved as in the display example of FIG. 5(h) in STEP S4. In the present example, body information required for ID registration comprises sex, age, height and weight.

In subsequent STEP S5, metabolic rates at each sleep stage, i.e. a basal metabolic rate (hereinafter referred to as "BMR") (kcal/min) and a sleep metabolic rate (hereinafter referred to as "SMR") (kcal/min), are calculated based on the above retrieved body information in the arithmetic section 8. Since these calculations are known, descriptions thereof are omitted.

Figure 5I:
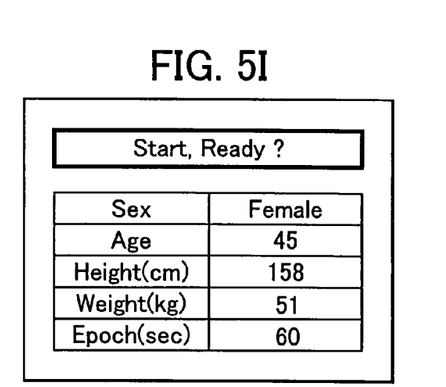
Figure 5J:
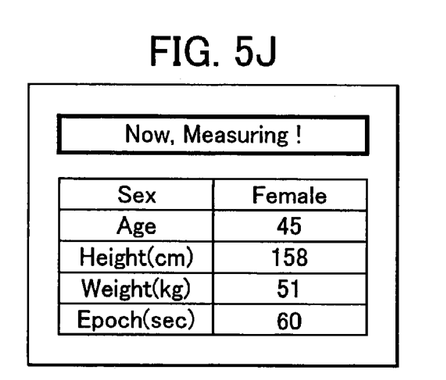

After completion of the calculations, guidance is displayed as in the display example of FIG. 5(i) and it is determined whether a measurement start operation has been performed in the operation section 11 in STEP S6. When the measurement start operation has not been performed, it is determined in STEP S7 whether predetermined time has elapsed. When the predetermined time has not elapsed, determination of the measurement start operation is repeated in STEP S6, while when the predetermined has elapsed, the power is turned off automatically, thereby ending the operations of the present apparatus 1. Meanwhile, when it has been determined in the above STEP S6 that the measurement start operation has been performed, a subroutine for calculation of consumed calories based on body oscillations during sleep that will be described later by use of the flowchart of FIG. 4 is executed. At that time, a message is displayed as in the display example of FIG. 5(j). After completion of the subroutine, it is determined in STEP S9 whether a measurement ending operation has been performed in the operation section 11. When the measurement ending operation has not been performed, the subroutine is executed again in STEP S8, while when the measurement ending operation has been performed, total calorie consumption during sleep is calculated from the consumed calories calculated by the subroutine executed in the above STEP S8 in the arithmetic section 8 in STEP S10. In subsequent STEP S11, the above total calorie consumption is displayed in the display section 12. Thereby, the present apparatus 1 ends the measurement.

Figure 7A:
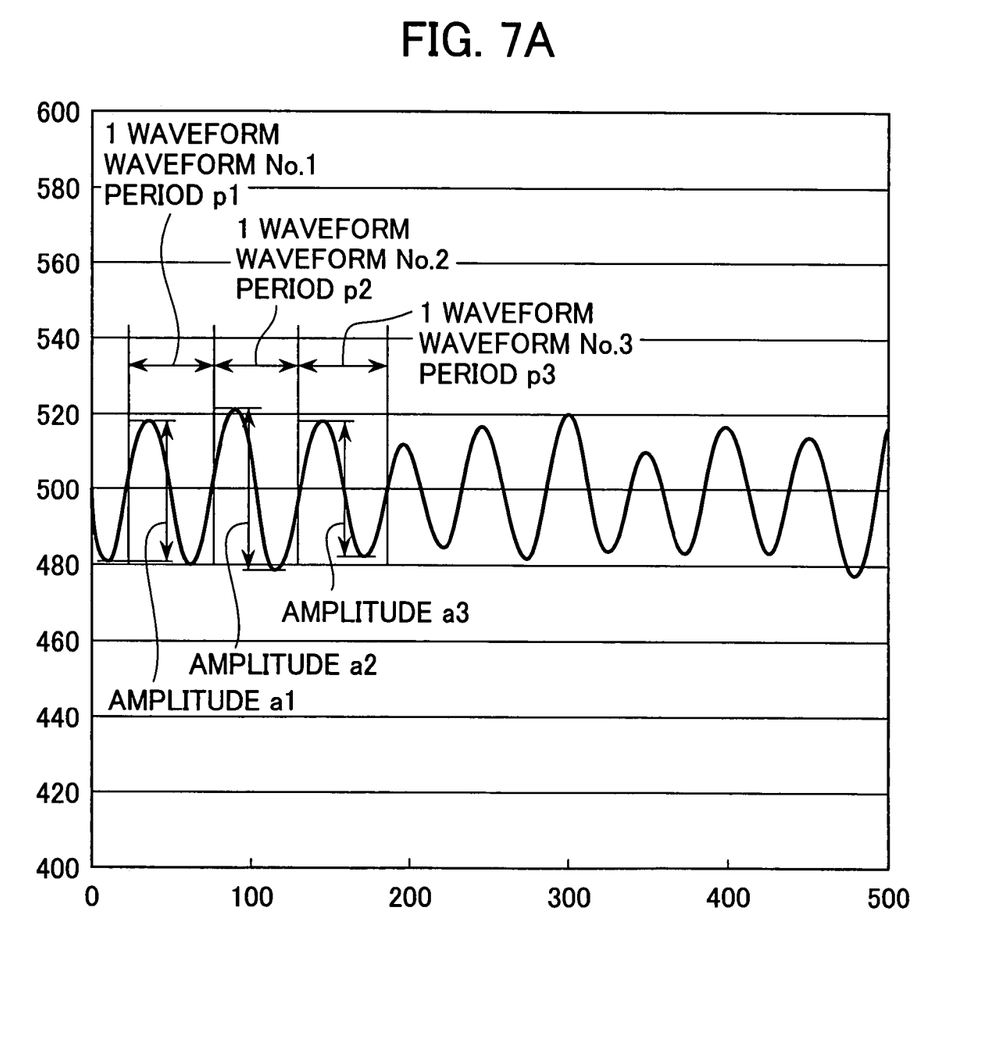
FIG. 7 is a diagram illustrating an example of the waveforms of body motion signals.
Figure 7B:
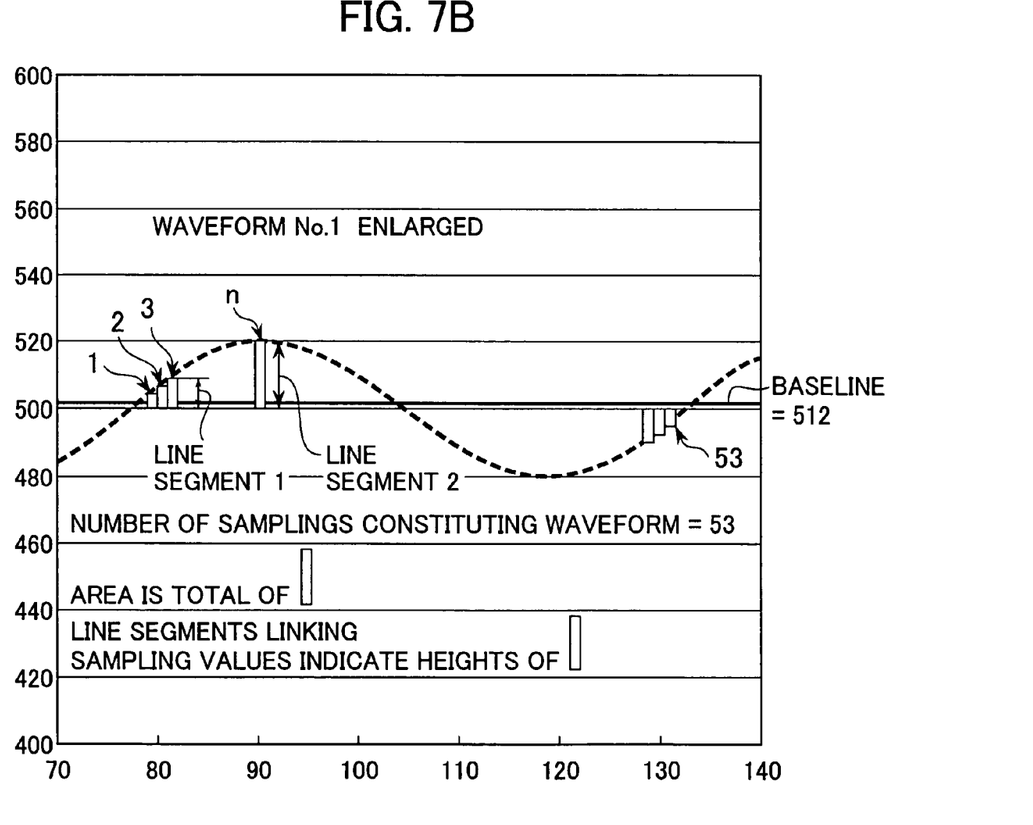

Next, operations in the subroutine for calculation of consumed calories based on body oscillations during sleep in the above STEP S8 of FIG. 3 will be described by use of the flowchart of FIG. 4. In STEP S21 of FIG. 4, the control section 4 in the CPU 9 controls the detection section 2 to sample data. In STEP S22, it is determined whether sampled data for a predetermined measurement epoch has been obtained. When the sampled data for the measurement epoch has not yet been obtained, data is sampled again in STEP S21, while when the sampled data for the measurement epoch has been obtained, body motion signals are determined in the determination section 5 based on the above sampled data which is a body oscillation signal detected by the detection section 2 in STEP S23. FIG. 7 illustrates an example of the waveforms of the body motion signals. In FIG. 7, a) is an overall view of the waveforms and b) is an enlarged view of a portion of the waveforms. The horizontal axis represents numeric values used to count the number of samplings of each waveform, and the vertical axis represents numeric values used for relative evaluation of the magnitude of the amplitude of each waveform. In particular, the numeric values of the vertical axis have substantially no significance except that around its center is set at 500 according to a relationship with the resolution of the AD converter to be described later. The determination of the body motion signals is performed by determining amplitudes (amplitudes a1, a2, a3, etc. in FIG. 7), periods (p1, p2, p3, etc. in FIG. 7) and the number of samplings which constitute one waveform (for example, the number of samplings which constitute a waveform with a waveform number 1 in FIG. 7 is 53) for waveforms (waveform numbers 1, 2, 3, etc. in FIG. 7) each of which is a waveform of exactly one period in the waveform of the body oscillation signal in the above measurement epoch, storing these data in the storage section 10 and determining signals which satisfy at least one of the following two conditions as the body motion signals. One of the conditions is that the amplitude of the above one waveform is equal to or larger than a predetermined threshold A0, and the other condition is that the variance of the amplitude of one waveform of interest and the amplitudes of waveforms before and after the waveform of interest is equal to or larger than a predetermined threshold B0. In this step, this determination is made on the whole waveform of the body oscillation signal in the measurement epoch, and the result of the determination on each waveform is stored in the storage section 10. At that time, waveforms determined as the body motion signals are stored, together with counts, in the counter provided in the CPU 9. The above thresholds A0 and B0 are thresholds for determining breathing/heartbeat oscillations and body motions and are values determined based on actually measured data.

Operations in STEPS S24 to S26 are operations repeated for each of the counts of the above stored body motion signals. That is, a body motion signal (one waveform) of one count is read from the storage section 10 in STEP S24, the body motion intensity of the above body motion signal is determined and the result of the determination is stored in the storage section 10 in association with the body motion signal of one count in STEP S25, and it is determined in STEP S26 whether body motion signals of all counts have been processed. If not, a body motion signal of the next count is read in STEP S24 so as to determine the intensity of the body motion signal of the next count.

Next, the above determination of the body motion intensity in STEP S25 will be described. In general, it is known that the intensities of exercises in one's life are classified as strong, normal, weak and very weak and each average calorie consumption is represented by the following expressions in which Wt represents a body weight value and Sex represents a sex coefficient (male: 0.001, female: 0) according to this classification.

Average Consumed Calories in Strong Exercise: $SPMR$ $(kcal/min) = Wt \times (0.156 + 12 \times Sex)$ Average Consumed Calories in Normal Exercise: NPMR (kcal/min)=Wt×(0.077+7×Sex)
Average Consumed Calories in Weak Exercise: WPMR (kcal/min)=Wt×(0.048+3×Sex)
Average Consumed Calories in Very Weak Exercise: VWPMR (kcal/min)=Wt×(0.025+2×Sex)

The above determination of the body motion intensity is based on this, and body motions are classified into 4 levels, i.e. strong body motion, normal body motion, weak body motion and very weak body motion, according to the predetermined magnitudes of the amplitudes of body motion signals, and the average consumed calories of each body motion correspond to the above average consumed calories of the intensities of exercises. For example, as shown in a body motion intensity determination table shown in FIG. 6, body motions are classified according to the ranges of the magnitude of the amplitude A of body motion signal. The numerical values of A0 to A3 and B0 are values determined based on actually measured data, and it is needless to say that A0<A1<A2<A3. For example, body motions observed during sleep include rolling over involving a large twisting motion of a whole body, stretching and contraction of pressed hands and legs, and coughing, and A0 to A3 and B0 are set arbitrarily stepwise by a manufacturer of the apparatus which runs these motions with actually measured data.

Further, at that time, Area(n) which is an area formed by line segments (line segment 1, line segment 2, etc. in FIG. 7) linking sampling values which constitute the above one waveform and a straight line (hereinafter referred to as "baseline") which links sampling reference values (in this case, points where the magnitudes of the sampling values are zero) which are bases for the magnitudes of the above sampling values is determined for each one waveform described above. The baseline is determined by an offset value which can be determined by the resolution of the AD converter used to analyze waveforms. For example, in the example shown in FIG. 7, since the AD converter has a resolution of $2^{10}$, the baseline is set at the middle point of $2^{10}$, i.e. 512. The above Area(n) is calculated from the total of absolute values of the differences between each sampling value Sample(n) (each sampled data in the measurement epoch) and the above baseline value Sample(0) in accordance with the following expression wherein t represents one sampling time.

$$\text{Area}(n)=\Sigma(|\text{Sample}(n)-\text{Sample}(0)|\times t)$$

Further, a sampling zone and the above area are determined for each body motion signal appearing in the measurement epoch, and the totals thereof are determined for each body motion intensity and stored in the storage section 10. The above sampling zone and the area of the zone are defined as follows.

Measurement Epoch (Total Sampling Period): Epoch(sec) and Total Area in the Period: Area(x)
Total of Sampling Zones of Strong Body Motion: Epoch1 (sec) and Total Area in the Zones: Area1
Total of Sampling Zones of Normal Body Motion: Epoch2 (sec) and Total Area in the Zones: Area2
Total of Sampling Zones of Weak Body Motion: Epoch3(sec) and Total Area in the Zones: Area3
Total of Sampling Zones of Very Weak Body Motion: Epoch4 (sec) and Total Area in the Zones: Area4

After completion of the above body motion determination on all counts in the measurement epoch, it is determined in STEP S27 whether there are body oscillations determined as body motions in the above measurement epoch. That is, it is determined whether the sleep state is a static sleep state involving only breathing/heartbeat oscillations or a dynamic sleep state involving body motions. When there are no body motions, the body oscillation signal in the measurement epoch is a breathing/heartbeat oscillation signal. That is, it is determined that the measurement epoch is in the static sleep state, and it is further determined in STEP S28 whether a coefficient (hereinafter simply referred to as "coefficient") corresponding to a reference value for calculating consumed calories of the body oscillation signal in the measurement epoch is stored in the storage section 10. When the coefficient is not stored, the above coefficient is calculated and set in the coefficient calculation section 6 in STEP S29, and STEP S31 to be described later, i.e. a consumed calorie calculation step, is performed, while when the coefficient is stored, the above STEP S31 is performed without performing the procedure in the above STEP S29.

Next, calculation and setting of the coefficient in the above STEP S29 will be described. First, the above coefficient is calorie consumption per unit area E_area (kcal/min) which is calculated based on Area0 which is an area formed by line segments linking sampling values and a baseline which is a basis for the magnitudes of the above sampling values and SMR (kcal/min) calculated and stored in STEP S5 of FIG. 3 in the above measurement epoch Epoch(sec) which is a sampling period in the above static sleep state. The above coefficient is calculated in accordance with the following expression.

$$E\_\text{area}=SMR\times\text{Epoch}/60(\text{sec/min})/\text{Area0}$$

The above area Area0 is calculated from the total of absolute values of the differences between each sampling value Sample (x) (each sampled data in the measurement epoch) and the above baseline value Sample(0) in accordance with the following expression wherein t represents one sampling time.

$$\text{Area0}=\Sigma(|\text{Sample}(x)-\text{Sample}(0)|\times t)$$

Meanwhile, when it has been determined in the above STEP S27 that there are body motions in the measurement epoch, it is determined in STEP S30, as in the above STEP S28, whether the above coefficient has been set, i.e. whether it is stored in the storage section 10. When the coefficient is stored, STEP S31, i.e. the consumed calorie calculation step is performed, while when the coefficient is not stored, the apparatus returns to the main routine shown in FIG. 3.

Consumed calories E in the measurement epoch in the above STEP S31 are represented by the following expression and are stored in the storage section 10 in advance.

$$E=E\_\text{area}\times(\text{Area}(x)-\text{Area1}-\text{Area2}-\text{Area3}-\text{Area4})+\\SPMR\times\text{Epoch1}/60+NPMR\times\text{Epoch2}/60+WPMR\times\\\text{Epoch3}/60+VWPMR\times\text{Epoch4}/60$$

That is, consumed calories when it has been determined in the above STEP S27 that there are no body motions in the measurement epoch, i.e. it has been determined that the measurement epoch is a static sleep state are calculated from E=E_area×Area(x) based on the above expression. Consequently, as described above, the consumed calories E in the measurement epoch are calculated in the consumed calorie calculation section 7 by having the coefficient E_area by the coefficient calculation section 6, the body weight and sex entered as body information and the sampling zone and area of the zone of each body motion based on the above body motion intensity determination available for calculation of the consumed calories E.

Although the total calorie consumption during sleep which is calculated in STEP S10 of the flowchart of FIG. 3 is simply displayed in the subsequent STEP S11, it may be used as a parameter for determining a so-called sleep period or sleep quality from the above total calorie consumption or, for example, transition in consumed calories in each measurement epoch.

Further, although the intensity of body motion is determined from the magnitude of the amplitude of body motion signal, the intensity of body motion may be alternatively determined from the magnitude of the period of body motion signal.

Further, although the area formed by the baseline of each body oscillation signal is calculated based on the differences between each sampled data and the baseline, it may be an integration value based on line segments linking adjacent sampled data and the baseline.

What is claimed is:

1. An apparatus for measuring calories consumed during sleep, comprising:
    an input section,
    a detection section,
    a calculation section,
    a determination section,
    a coefficient calculation section,
    a consumed calorie calculation section, and
    a storage section,
    wherein
    the input section inputs the body information of a subject,
    the detection section detects body oscillations during sleep and generates body oscillation signals responsive to the body oscillations, and comprises a mat to detect body oscillations including breathing and heartbeat oscillations and body motions of a human body lying on bedding disposed between the human body and the mat,
    the calculation section calculates consumed calories based on the body oscillations,
    the determination section determines whether each signal of body oscillation during sleep is a signal of breathing/heartbeat oscillation or a signal of body motion and determines the intensity of the body motion based on the magnitude of the signal of body motion,
    the coefficient calculation section calculates a coefficient which is a reference value for calculating calories consumed during sleep, based on the signals in a given period of breathing/heartbeat oscillation and a sleep metabolic rate which is obtained based on the input body information,
    the consumed calorie calculation section calculates calories consumed during sleep, based on consumed calories according to the magnitude of the signal of breathing/heartbeat oscillation, consumed calories according to the magnitude of the signal of body motion, and the coefficient,
    the storage section stores at least thresholds for making determinations in the determination section, an arithmetic expression for calculating the coefficient, and an arithmetic expression for calculating the calories consumed during sleep in advance,
    the consumed calorie calculation section calculates an area formed between the waveform of each signal and a baseline which is a basis for waveform formation as the magnitude of each signal, and
    the consumed calorie calculation section calculates consumed calories according to the magnitude of the signal of body motion, based on the total of sampling zones for each body motion intensity and the total of the areas.

2. The apparatus of claim 1, wherein the determination section is adapted to determine whether each signal of body oscillation during sleep is a signal of breathing or heartbeat oscillation or a signal of body motion by determining signals which satisfy at least one of two conditions as the signal of body motion, one of the conditions being that the amplitude of the waveform of exactly one period of the signal of body oscillation is equal to or larger than a predetermined threshold, and the other condition being that the variance of the amplitude of the waveform of exactly one period of the signal of body oscillation and amplitudes of waveforms before and after the waveform is equal to or larger than another predetermined threshold.

* * * * *